United States Patent [19]

Smith et al.

[11] Patent Number: 5,604,231
[45] Date of Patent: Feb. 18, 1997

[54] PHARMACEUTICAL COMPOSITIONS FOR PREVENTION AND TREATMENT OF ULCERATIVE COLITIS

[76] Inventors: Carr J. Smith, 5548 Moravian Heights La., Clemmons, N.C. 27012; Patrick M. Lippiello, 1233 Arboretum Dr., Lewisville, N.C. 27023; Merouane Bencherif, 5437-B Countryside Dr., Winston-Salem, N.C. 27105; William S. Caldwell, 1270 Yorkshire Rd., Winston-Salem, N.C. 27106; Gary M. Dull, 1175 Sequoia Dr., Lewisville, N.C. 27023

[21] Appl. No.: 364,980

[22] Filed: Jan. 6, 1995

[51] Int. Cl.$^6$ .......................... A01N 43/54; A61K 31/44
[52] U.S. Cl. ........................ 514/256; 514/277; 514/357
[58] Field of Search ................................ 514/256, 277, 514/357

[56] References Cited

U.S. PATENT DOCUMENTS

| | | |
|---|---|---|
| 5,312,818 | 5/1994 | Rubin et al. . |
| 5,324,738 | 6/1994 | Dinan et al. . |
| 5,331,013 | 7/1994 | Hakan et al. . |
| 5,340,801 | 8/1994 | Ewing et al. . |

OTHER PUBLICATIONS

*Cecil Testbook of Medicine*, 19th Edition, pp. 699–708, Ed. by Wyngaarden et al. Dec. 1992.
Amaral–Corfield, C. et al., "The glycoconjugate content of rectal biopsies from normal and ulcerative colitic non--smokers", *Med. Sci. Res.*, vol. 19, pp. 309–310 Dec. 1991.
Barton, J. et al., "Mucosalimmunodeficiency in smokers, and in patients with epithelial head and neck tumors", *Gut*, vol. 31. 378–382 Dec. 1990.
Boyko, E. et al., "Effects of Cigarette Smoking on the Clinical Course of Ulcerative Colitis", *Scandinavian Journal of Gastroenterology*, vol. 23 (9), pp. 1147–1152 Dec. 1988.
Calkins, B., "A Meta–Analysis of the Role of Smoking in Inflammatory Bowerl Disease", *Digestive Diseases and Sciences*, vol. 34 (12), pp. 1841–1854 Dec. 1989.
Castella, H., "Non–smoking: a feature of ulcerative colitis", *BMJ*, vol. 284, p. 1706 Dec. 1982.
Cope, G. et al., "Cigarette smoking and intestinal defences", *Gut*, vol. 33, 721–723 Dec. 1992.
Guslandi, M. et al., "Steroid–Sparing Effect of Transdermal Nicotine in Ulcerative Colitis", *J. Clin. Gastroenterol.*, vol. 18 (4), pp. 347–350 Jun. 1994.
Jameson, J. et al., "The Effect of Smoking on Colonic Pressure Activity", *Gastroenterology*, vol. 104 (4) (Suppl.), p. A527 Dec. 1993.
Jick, H. et al., "Cigarette Smoking and Ulcerative Colitis", *New England Journal of Medicine*, vol. 308, pp. 261–263 Dec. 1983.
Katchinski, B., "Smoking and Sugar Intake in Ulcerative Colitis", *AGA Abstracts*, vol. 98 (5) (part 2), p. A180 Dec. 1990.
Kirsner, J. et al., "Recent Developments in Nonspecific Inflammatory Bowel Disease", *New England Journal of Medicine*, vol. 306 (13), pp. 775–784 Dec. 1982.
Lashner, B., "Conspectus Inflammatory Bowel Disease, Family Patterns and Risk Factors", *Comprehensive Therapy*, vol. 18 (8), pp. 2–4 Dec. 1992.
Lashner, B. et al., "Testing Nicotine Gum for Ulcerative Colitis Patients", *Digestive Diseases and Sciences*, vol. 35 (7), pp. 827–832 Dec. 1990.
Macpherson, A. et al, "Inflammatory bowel disease of mice–and men?", *The Lancet*, vol. 343, pp. 130–131 Jan. 1994.
Motley, R. et al., "Smoking, eicosanoids and ulcerative colitis", *J. Pharm. Pharmacol.*, vol. 42, pp. 288–289 Dec. 1990.
Perera D. et al., "Smoking and ulcerative colitis", *British Medical Journal*, vol. 288, p. 1533 Dec. 1984.
Pullan, R. et al., "Transdermal Nicotine for Active Ulcerative Colitis", *New England Journal of Medicine*, vol. 330 (12), pp. 811–815 Mar. 1994.
Prytz, H. et al., "Does Smoking Tighten the Gut?", *Scand. J. Gastroenterol.*, vol. 24, pp. 1084–1088 Dec. 1989.

(List continued on next page.)

*Primary Examiner*—James J. Seidleck
*Assistant Examiner*—John M. Cooney, Jr.

[57] ABSTRACT

Patients suffering from or susceptible to an idiopathic chronic inflammatory bowel disease (e.g., ulcerative colitis) are treated with pharmaceutical compositions. Those patients are treated by administration of an effective amount of aryl substituted aliphatic compound, an aryl substituted olefinic amine compound or an aryl substituted acetylenic compound. Exemplary compounds are (E)-4-(5-pyrimidinyl)-3-butene-1-amine, (E)-4-[3-(5-methoxypyridin)yl]-3-butene-1-amine, (E)-N-methyl-4-(5-pyrimidinyl)-3-butene-1-amine, (E)-N-methyl-4-[3-(5-methoxypyridin)yl]-3-butene-1-amine, (E)-metanicotine, (Z)-metanicotine, N-methyl-(3-pyridinyl)-butane-1-amine, N-methyl-4-(3-pyridinyl)-3-butyne-1-amine and (E)-N-methyl-4-[3-(6-methylpyrindin)yl]-3-butone-1-amine.

21 Claims, No Drawings

OTHER PUBLICATIONS

Rhodes, J. et al., "Smoking: Good or Bad for Inflammatory Bowel Disease?", *Gastroenterology*, vol. 106 (3), pp. 807–810 Mar. 1994.

Roberts, C. et al., "Non–smoking: a feature of ulcerative colitis", *BMJ*, vol. 285, p. 440 Dec. 1982.

Rudra, T. et al., "Does Smoking Improve Colitis?", *Scand. J. Gastroenterol.*, vol. 24 (suppl. 170), pp. 61–63 Dec. 1989.

Samuelsson, S. et al., "Risk factors for extensive ulcerative colitis and ulcerative proctitis: a population based case–control study", *Gut*, vol. 32, pp. 1526–1530 Dec. 1991.

Shivananda, S. et al., "Epidemiology of inflammatory bowel disease", *Current Opinion in Gastroenterology*, vol. 9, pp. 560–565 Dec. 1993.

Srivastava, E. et al., "Effect of ulcerative colitis and smoking on rectal blood flow", *Gut*, vol. 31, pp. 1021–1024 Dec. 1990.

Srivastava, E. et al., "Smoking, humoral immunity, and ulcerative colitis", *Gut*, vol. 32, pp. 1016–1019 Dec. 1991.

Srivastava, E. et al., "Transdermal nicotine in active ulcerative colitis", *European Journal of Gastroenterology & Hepatology*, vol. 3, pp. 815–818 Dec. 1991.

Srivastava, E. et al., "Effect of Nicotine and Cotinine on the Production of Oxygen Free Radicals by Neutrophils in Smokers and Non-smokers", *Human Toxicol.*, vol. 8, pp. 461–463 (Dec. 1989).

Thomas and Rhodes, *International Symposium on Nicotine*, S38, Jul. 1994, eds. Clarke et al.

Zijlstra, F. et al., "Effect of nicotine on rectal mucus and mucosal eicosanoids", *Gut*, vol. 35, pp. 247–251 Feb. 1994.

Physicians' Desk Reference, 48 Edition, pp. 1112–1113 (Dec. 1994), "Dipentum".

Physicians' Desk Reference, 48 Edition, pp. 1805–1806 (Dec. 1994), "Asacol".

Physicians' Desk Reference, 48 Edition, pp. 2307–2309 (Dec. 1994), "Rowasa".

PHARMACEUTICAL COMPOSITIONS FOR PREVENTION AND TREATMENT OF ULCERATIVE COLITIS

BACKGROUND OF THE INVENTION

The present invention relates to compounds having pharmaceutical properties, and in particular, to compounds useful for preventing and treating inflammatory bowel diseases. More specifically, the present invention relates to a method for treating patients suffering from an idiopathic chronic inflammatory bowel disease (e.g., ulcerative colitis), and in particular, to compositions of matter useful as pharmaceutical compositions in the prevention and treatment of such a disease.

Idiopathic ulcerative colitis (UC) is a recurrent acute and chronic ulcero-inflammatory disorder principally affecting the rectum and left colon, but sometimes the entire large bowel. See, Kirsner et al., *N. Engl. J. Med.*, Vol. 306, pp.775-837 (1982). UC encompasses a spectrum of diffuse, continuous, superficial inflammation of the colon, which begins in the rectum and extends to a variable proximal level. See, *Cecil Textbook Of Medicine*, 19th Edition, p. 699, Ed. by Wyngaarden et al. (1992). Matters relating to the etiology (i.e., definitive etiopathogenesis is not kayown), epidemiology, pathogenesis, pathology, symptoms, diagnosis (e.g., endoscopy and radiography), and complications (e.g., cancer, intestinal complications such as rectal bleeding and toxic megacolon, and extraintestinal complications such as anemia and leukocytosis) are set forth in relatively complete detail in *Cecil Textbook of Medicine* (supra).

The manner in which UC is treated can vary, and typically the medical treatment depends upon the severity of the symptoms exhibited by the patient. Corticosteroids (e.g., prednisone), antibiotics (e.g., tetracycline, sulfa-trimethoprim, metronidazole and cephalexin) and inunnunosuppressivcs (e.g., 6-mercaptopurine and azathioprine) often are used for treating UC. Anti-inflammatory agents (e.g., sulfasalazine and mesalamine) are effective to some degree in some patients for the treatment of acute UC. Certain anti-inflammatory agents are available commercially as Asacol from Rolm Pharma G.m.b.H., Dipentum from Kabi Pharmacia AB and Rowasa from Solvay Pharmaceuticals. In more severe cases or when the anti-inflammatory agents fail to relieve the symptoms of UC, surgical procedures are used. Typical surgical procedures include colectomy, proctocolectomy and ileostomy. See, *Cecil Textbook of Medicine* (supra). Other treatment methods for gastrointestinal disorders have been proposed in U.S. Pat. Nos. 5,312,818 to Rubin et al, 5,324,738 to Dinan et al., 5,331,013 to Ahlman et al. and 5,340,801 to Ewing et al.

Epidemiology studies indicate a possibility that lifestyle may play a role in the development of UC. See, Shievananda et al., Current opinion in Gastroenterology, Vol. 9, pp.560-565 (1993). Factors such as the environment and cigarette smoking have been examined for associations with UC. See, Lashnet, Digestive Diseases and Sciences, Vol. 35 (7), pp. 827-832 (1992) and Calkins, Digestive Diseases and Sciences, Vol. 34 (12), pp. 1841-1854 (1989). Several clinical studies have reported that cigarette smoking improves the course of UC. See, Rudra et al., *Scand. J. Gastroenterol*, Vol. 24 (Suppl 170), pp. 61-63 (1989); and Thomas and Rhodes, *International Symposium on Nicotine*, S38, 1994, eds. Clarke et al. Several hypotheses have been proposed to explain the inverse relationship between cigarette smoking and UC. These hypotheses include smoking-associated changes in colonic mucus (Amaral-Corfield et al., *Med. Sci. Res.*, Vol. 19, pp. 309-310 (1991 )); intestinal permeability (Prytz et al., *Scand. J. Gastroenterol*, Vol. 24, pp. 1084-1088 (1989)); rectal blood flow (Srivastava et al., *Gut*, Vol. 31, pp. 1021-1024 (1990)); immunoglobulin secretion (Barton et al., *Gut*, Vol. 31, pp. 378-382 (1990); Srivastava et al., *Eur. J. Gastroenterol. & Hepatol.*, Vol. 3, pp. 815-818 ( 1991)); and antioxidant defenses (Cope et al., Gut, Vol. 33, pp.721-723 (1992)). Nicotine has been tested as a treatment for active UC. See, Srivastava et al., *Eur. J. Gastroenterol. & Hepatol.*, Vol. 3, pp. 815 -818 ( 1991 )). Improvement of UC symptoms was also observed following the use of nicotine gum (Lashner et al., *Digestive Diseases and Sciences*, Vol. 35(7), pp. 827-832 (1990)) and nicotine patch (Pullan et al., *N. Engl. J. Med.*, Vol. 330, pp. 811-815 (1994)).

It would be desirable to provide a pharmaceutical composition useful for the prevention and treatment of inflammatory bowel diseases. It would be highly beneficial to provide individuals suffering from certain inflammatory bowel diseases with interruption of the symptoms of those diseases by the administration of a compound which has nicotinic pharmacology and which has a beneficial effect upon the functioning of the gastrointestinal tract, but which does not provide any significant associated side effects (e.g., increased heart rate and blood pressure) attendant with interaction of that compound with cardiovascular sites. It would be highly desirable to provide a pharmaceutical composition incorporating a compound which interacts with nicotinic receptors which have the potential to affect the functioning of the gastrointestinal tract, but which does not significantly affect those receptors which have the potential to induce side effects (e.g., appreciable pressor cardiovascular effects and appreciable activity at skeletal muscle sites).

SUMMARY OF THE INVENTION

The present invention relates to aryl substituted aliphatic amine compounds, aryl substituted olefinic amine compounds and aryl substituted acetylenic amine compounds.

The present invention relates to a method for providing prevention or treatment of an inflammatory bowel disease, such as ulcerative colitis. The method involves administering to a patient an effective amount of a compound of the present invention.

The present invention, in another aspect, relates to a pharmaceutical composition comprising an effective amount of a compound of the present invention. Such a pharmaceutical composition incorporates a compound which has the capability of interacting with nicotinic receptor sites of a patient, and hence has the capability of acting as a therapeutic in the prevention or treatment of an inflammatory bowel disease, such as ulcerative colitis.

The pharmaceutical compositions of the present invention are useful for the prevention and treatment of inflammatory bowel diseases. The pharmaceutical compositions provide therapeutic benefit to individuals suffering from certain inflammatory bowel diseases in that the compounds within those compositions have the potential to (i) exhibit nicotinic pharmacology, (ii) prevent and suppress the symptoms associated with those diseases, and (iii) not provide appreciable adverse side effects (e.g., significant increases in blood pressure and heart rate, and significant effects upon skeletal muscle). The pharmaceutical compositions of the present invention are believed to be safe and effective with regards to prevention and treatment of inflammatory bowel diseases.

DETAILED DESCRIPTION OF THE PREFERRED EMBODIMENTS

The present invention, in one aspect, relates to certain compounds having the formula:

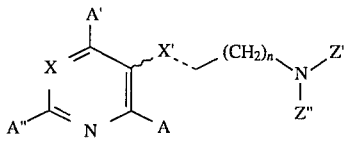

where X is nitrogen or carbon bonded to a substituent species characterized as having a sigma m value greater than 0, often greater than 0.1, generally greater than 0.2 and even greater than 0.3; less than 0 and generally less than −0.1; or 0; as determined in accordance with Hansch et al., *Chem. Rev.*, Vol. 91, pp. 165–195 (1991); n is an integer which can range from 1 to 5, preferably from 1 to 3, and most preferably is 2 or 3; Z' and Z" individually represent hydrogen or lower alkyl (e.g., alkyl containing one to five carbon atoms, such as methyl, ethyl or isopropyl), and preferably at least one of Z' and Z" is hydrogen; A, A' and A" individually represent hydrogen, alkyl (e.g., lower straight chain or branched alkyl, including $C_1$–$C_7$, but preferably methyl or ethyl) or halo (e.g., F, Cl, Br or I); the dashed line in the structure represents a C—C single bond, a C—C double bond or a C—C triple bond; the wavy line in the structure represents a cis (Z) or trans (E) form of the compound when the dashed line is a C—C double bond; and X' represents $CH_2$ when the dashed line is a C—C single bond, CH when the dashed line is a C—C double bond, and C when the dashed line is a C—C triple bond. X includes N, C—H, C—F, C—Cl, C—Br, C—I, C—NR'R", C—$CF_3$, C—OH, C—CN, C—SH, C—$SCH_3$, C—$N_3$, C—$SO_2CH_3$, C—OR', C—C(=O)N R'R", C—NR'C(=O)R', C—C(=O)OR', C—OC(=O)R', C—OC(=O)NR'R" and C—NR'C(=O)OR' where R' and R" are individually hydrogen or lower alkyl (e.g., alkyl containing one to five carbon atoms, preferably methyl or ethyl). When X represents a carbon atom bonded to a substituent species, that substituent species often has a sigma m value which is between about −0.3 and about 0.75, and frequently between about −0.25 and about 0.6. In certain circumstances when X represents a carbon atom bonded to a substituent species, the dashed line is a C—C double bond and the compound has the trans (E) form, the substituent species is characterized as having a sigma m value not equal to 0. Particularly when the dashed line is a C—C double bond, the compound has the trans (E) form, A, A', A" and Z' all are hydrogen, n is 2, and Z" is methyl, the substituent species is characterized as having a sigma m value not equal to 0. In addition, it is highly preferred that A is hydrogen, it is preferred that A' is hydrogen, and normally A" is hydrogen. Generally, both A and A' are hydrogen; sometimes A and A' are hydrogen, and A" is methyl or ethyl; and often A, A' and A" are all hydrogen. One representative compound is N-methyl-4-(3-pyridinyl)-butane-1-amine for which for which the dashed line is a C—C single bond, X' is $CH_2$, X is C—H, n is 2, and A, A', A" and Z' each are hydrogen, and Z" is methyl. Another representative compound is N-methyl-4-(3-pyridinyl)-3-butyne-1-amine for which for which the dashed line is a C—C triple bond, X' is C, X is C—H, n is 2, and A, A', A" and Z' each are hydrogen, and Z" is methyl. Other representative compounds are (Z)-metanicotine and (E)-metanicotine, for which the dashed line is a C—C double bond, X' is CH, n is 2, and A, A', A" and Z' each are hydrogen, and Z" is methyl. Of particular interest are compounds having the formula:

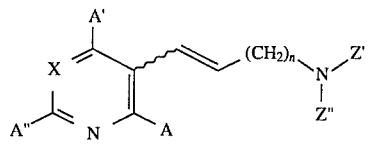

where n, X, A, A', A", Z' and Z" are as defined hereinbefore, and those compounds can have the cis (Z) or trans (E) form. For such compounds of particular interest, X most preferably is nitrogen or carbon bonded to a substituent species characterized as having a sigma m value greater than 0, often greater than 0.1, generally greater than 0.2 and even greater than 0.3; less than 0 and generally less than −0.1; or 0. One representative compound is (E)-4-(5-pyrimidinyl)-3-butene-1-amine for which X is N, n is 2, and A, A', A", Z' and Z" each are hydrogen. Another representative compound is (E)-4-[3-(5-methoxypyridin)yl]-3-butene-1-amine for which X is C—$OCH_3$, n is 2, and A, A', A", Z' and Z" each are hydrogen. Another representative compound is (E)-N-methyl-4-(5-pyrimidinyl)-3-butene-1-amine for which X is N, n is 2, A, A', A", and Z' are each hydrogen, and Z" is methyl. Another representative compound is (E)-N-methyl-4-[3-(5-methoxypyridin)yl]-3-butene-1-amine for which X is C—$OCH_3$, n is 2, and A, A', A", and Z' are each hydrogen, and Z" is methyl. Another representative compound is (E)-4-[3-(5-ethoxypyridin)yl]-3-butene-1-amine for which X is C—$OCH_2CH_3$, n is 2, and A, A', A", Z' and Z" each are hydrogen. Another representative compound is (E)-N-methyl-4-[3-(5-ethoxypyridin)yl]-3-butene-1-amine for which X is C—$OCH_2CH_3$, n is 2, A, A', A" and Z' each are hydrogen, and Z" is methyl. Another representative compound is (E)-4-[3-(5-aminopyridin)yl]-3-butene-1-amine for which X is C—$NH_2$, n is 2, and A, A', A", Z' and Z" each are hydrogen. Another representative compound is (E)-N-methyl-4-[3-(5-aminopyridin)yl]-3-butene-1-amine for which X is C—$NH_2$, n is 2, A, A', A" and Z' each are hydrogen, and Z" is methyl. Another representative compound is (E)-4-[3-(5-bromopyridin)yl]-3-butene-1-amine for which X is C—Br, n is 2, and A, A', A", Z' and Z" each are hydrogen. Another representative compound is (E)-N-methyl-4-[3-(5-bromopyridin)yl]-3-butene-1-amine for which X is C—Br, n is 2, A, A', A" and Z' each are hydrogen, and Z" is methyl. Another representative compound is (E)-4-[3-(5-methoxy-6-methylpyridin)yl]-3-butene-1-amine for which X is C—$OCH_3$, n is 2, A" is methyl, and A, A', Z' and Z" each are hydrogen. Another representative compound is (E)-N-methyl-4-[3-(5-methoxy-6-methylpyridin)yl]-3-butene-1-amine for which X is C—$OCH_3$, n is 2, A" and Z" each are methyl, and A, A' and Z' each are hydrogen. Another representative compound is (E)-N-methyl-4-[3-(6-methylpyridin)yl]-3-butene-1-amine for which X is C—H, n is 2, A" and Z" each are methyl, and A, A' and Z' each are hydrogen. Another representative compound is (E)-4-[3-(6-methylpyridin)yl]-3-butene-1-amine for which X is C—H, n is 2, A" is methyl, and A, A', Z' and Z" each are hydrogen. Another representative compound is (E)-N-methyl-5-[3-pyridinyl]-4-pentene-1-amine for which X is C—H, n is 3, Z" is methyl, and A, A', A" and Z' are each hydrogen. Another representative compound is (E)-N-(2-propyl)-4-[3-pyridynyl]-3-butene-1-amine for which X is C—H, n is 2, Z" is isopropyl, and A, A', A" and Z' are each hydrogen.

The manner in which aryl substituted aliphatic amine compounds of the present invention are synthetically produced can vary. Preparation of various aryl substituted aliphatic amine compounds can be carried out using the types of techniques disclosed by Rondahl, *Acta Pharm.*

*Suec.*, Vol. 13, pp. 229–234 (1976). Certain metanicotine-type compounds that possess a saturated side chain rather than an olefinic side chain can be prepared by hydrogenation of the corresponding metanicotine-type compounds or the corresponding acetylenic precursors. For example, dihydrometanicotine can be prepared by hydrogenation of (E)-metanicotine as described by Kamimura et al., *Agr. Biol. Chem.*, Vol. 27, No. 10, pp. 684–688 (1963).

The manner in which aryl substituted acetylenic amine compounds of the present invention are synthetically produced can vary. For example, an aryl substituted acetylenic amine compound, such N-methyl-4-(3-pyridinyl)-3-butyne-1-amine, can be prepared using a number of synthetic steps: (i) conversion of 3-pyridinecarboxaldehyde to a 1,1-dihalo-2-(3-pyridinyl)-ethylene using a carbon tetrahalide and triphenylphosphine, (ii) side chain elaboration of this intermediate by reaction with butyl lithium and ethylene oxide, affording 4-(3-pyridinyl)-3-butyn-1-ol, (iii) conversion of this intermediate to its methanesulfonate ester, and (iv) mesylate displacement with methyl amine, affording N-methyl-4-(3-pyridinyl)-3-butyne-1-amine.

The manner in which aryl substituted olefinic amine compounds of the present invention are synthetically produced can vary. (E)-metanicotine can be prepared using the techniques set forth by Löffler et al., *Chem. Ber.*, Vol. 42, pp. 343 1–3438 (1909) and Laforge, *J.A.C.S.*, Vol. 50, p. 2477 (1928). Certain novel 6-substituted metanicotine-type compounds can be prepared from the corresponding 6-substituted nicotine-type compounds using the general methods of Acheson et al., *J. Chem. Soc., Perkin Trans.* 1, Vol. 2, pp. 579–585 (1980). The requisite precursors for such compounds, 6-substituted nicotine-type compounds, can be synthesized from 6-substituted nicotinic acid esters using the general methods disclosed by Rondahl, *Acta Pharm. Suet.*, Vol. 14, pp 113–118 (1977). Preparation of certain 5-substituted metanicotine-type compounds can be accomplished from the corresponding 5-substituted nicotine-type compounds using the general method taught by Acheson et al., *J. Chem. Soc., Perkin Trans.* 1, Vol. 2, pp. 579–585 (1980). The 5-halo nicotine-type compounds (e.g., fluoro and bromo nicotine-type compounds) and the 5-amino nicotine-type compounds can be prepared using the general procedures disclosed by Rondahl, *Act. Pharm. Suec.*, Vol. 14, pp. 113–118 (1977). The 5-trifluoromethyl nicotine-type compounds can be prepared using the techniques and materials set forth in Ashimori et al., *Chem. Pharm. Bull.*, Vol. 38(9), pp. 2446–2458 (1990) and Rondahl, *Acta Pharm. Suec.*, Vol. 14, pp. 113–118 (1977). Furthermore, preparation of certain rectanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, cemain metanicotine-type compounds can be prepared by subjecting a 3-halo substituted, 5-substituted pyridine compound or a 5-halo substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., *J. Org. Chem.*, Vol. 43(15), pp. 2947–2949 (1978) and Malek et al., *J. Org. Chem.*, Vol. 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group affords the desired metanicotine-type compound. There are a number of different methods for providing (Z)-metanicotine-type compounds. In one method, (Z)-metanicotine-type compounds can be synthesized from nicotine-type compounds as a mixture of E and Z isomers; and the (Z)-metanicotine-type compounds can then be separated by chromatography using the types of techniques disclosed by Sprouse et al., Abstracts of Papers, p. 32, Coresta/TCRC Joint Conference (1972). In another method, (Z)-metanicotine can be prepared by the controlled hydrogenation of the corresponding acetylenic compound (e.g., N-methyl-4-(3-pyridinyl)-3-butyne-1-amine). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively.

A representative compound, (E)-N-methyl-4-[3-(5-bromopyridin)yl]-3-butene-1-amine, can be synthesized using the following representative procedure. 5-Bromonicotine (0.018 mole) in 10 ml of methylene chloride dried over phosphorous pentaoxide has a solution of ethyl chloroformate (0.018 mole) in 10 mL of similarly dried methylene chloride added dropwise over 10 to 15 minutes. The resulting mixture then is refluxed under nitrogen atmosphere for about 3 hours. Then, the methylene chloride is removed using a rotary evaporator, and the remaining material is distilled under reduced pressure to yield a N-ethylcarbamate derivative of 5-bromometanicotine product as a thick liquid which has a boiling point of 182° C. at 0.04 mm Hg. This product (0.08 mole) is then refluxed for several hours in 15 ml of concentrated aqueous hydrochloric acid. The resulting reaction mixture was cooled and basified to pH 8–9 using concentrated aqueous sodium hydroxide while the mixture is maintained at a temperature of about 0° C. The resulting product is extracted four times with 20 ml quantities of chloroform, and the combined collected fractions are dried over anhydrous sodium sulfate. Then, the chloroform is removed using a rotary evaporator, and the remaining material is distilled under reduced pressure to yield the (E)-N-methyl-4-[3-(5-bromopyridin)yl]-3-butene-1-amine product as a colorless liquid which has a boiling point of 115° C. at 0.04 mm Hg. That product can be converted to a fumarate salt, which has a melting point of 148°–150° C.

A representative compound, (E)-N-methyl-5-[3-pyridinyl]-4-pentene-1-amine, can be synthesized using the following representative procedure. A solution of N-methyl anabasine (0.011 mole) in 100 mL methylene chloride is added dropwise into a slight molar excess of ethyl chloroformate in 100 mL methylene chloride under nitrogen atmosphere in a flask equipped with a condenser. Then, the mixture is refluxed for about 3 hours. Then, the methylene chloride is removed using a rotary evaporator, and the remaining material is distilled using a short-path distillation apparatus to yield N-ethylearbamate of trans-homometanicotine product as a colorless liquid which has a boiling point of 170°–172° C. at 1 mm Hg. This product (0.012 mole) is dissolved in 50 mL concentrated aqueous hydrochloric acid, and the resulting mixture is refluxed overnight. The reaction mixture then is cooled. The resulting product is extracted four times with 20 mL quantities of chloroform, and the combined collected fractions are dried over anhydrous sodium sulfate. Then, the chloroform is removed using a rotary evaporator, and the remaining material is distilled under reduced pressure to yield the (E)-N-methyl-5-[3-pyridinyl]-4-pentene-1-amine product as a colorless liquid which has a boiling point of 81°–82° C. at 4 mm Hg. That product can be converted to a fumarate salt, which has a melting point of 139°–140° C.

A representative compound, (E)-N-(2-propyl)-4-[3-pyridinyl]-3-butene-1-amine, can be synthesized using the following representative procedure. (E)-4-[3-pyridynyl]-3-butene-1amine (0.5 millimole) is prepared according to the procedure of Heck, *J. Org. Chem.*, Vol. 43, pp. 2947 (1978), combined with 2-iodopropane (0.525 millimole) and potassium carbonate (1 millimole), and refluxed in 30 mL tetrahydrofuran for 36 hours. Then, the tetrahydrofuran is removed using a rotary evaporator and 5 mL ethyl ether is added to the remaining residue. Filtration followed by concentration on a rotary evaporator yields a brown oil which can be purified by column chromatography followed by distillation under reduced pressure (138°–140° C. at 0.25 mm Hg ) to yield the (E)-N-(2-propyl)-4-[3-pyridynyl]-3-butene-1-amine product.

A representative compound, (E)-N-methyl-4-[3-(5-aminopyridin)yl]-3-butene-1-amine, can be synthesized using the following representative procedure. 5- Amino nicotine (1 millimole) is prepared according to the procedure of Rondahl, *Acta. Pharm. Suec.*, Vol. 14, pp. 113 (1977), combined with phthalic anhydride (1 millimole), and refluxed in 3 mL toluene for 16 hours using a Dean-Stark trap. The reaction mixture is cooled to ambient temperature and the toluene is removed using a rotary evaporator. To the remaining residue is added 2 mL methylene chloride, followed by dropwise addition of ethyl chloroformate (1.1 millimole) under nitrogen atmosphere. The resulting mixture is refluxed for 8 hours, cooled to ambient temperature, and concentrated on a rotary evaporator. The resulting viscous oil is heated to 160° C. under vacuum for one hour, and then cooled to ambient temperature. Then, 10 mL of a 10 percent aqueous solution of sodium bicarbonate is added to the reaction mixture. That mixture then is extracted three times with 15 mL portions of chloroform. The combined portions then are dried over anhydrous potassium carbonate. Filtration followed by lo evaporation of chloroform yields a pale brown oil. This oil is dissolved in 1 mL tetrahydrofuran followed by 2 mL of a solution 2 parts methyl amine in 3 parts water. This mixture is stirred for 10 hours. Then, tetrahydrofuran and excess methyl amine are removed using a rotary evaporator. Concentrated aqueous hydrochloric acid (5 mL) is added to the reaction mixture followed by reflux for several hours. The acidic solution, after cooling to ambient temperature, is extracted three times with 10 mL portions of ethyl acetate. Then, the acidic solution is basified using potassium carbonate and then sodium hydroxide. The basic solution then is extracted four times with 10 mL portions of n-butyl alcohol. The combined extracts are dried over anhydrous magnesium sulfate. Filtration, followed by concentration on a rotary evaporator yields the (E)-N-methyl-4-[3-(5-aminopyridin)yl]-3-butene-1-amine product as a dark brown oil. The product can be purified by column chromatography using a chloroform:methanol:triethylamine (60:20:20) solvent system as an eluent.

The present invention relates to a method for providing prevention of an inflammatory bowel disease, such as UC, to a patient susceptible to such a disease, and for providing treatment to a patient suffering from an inflammatory bowel disease, such as UC. In particular, the method comprises administering to a patient an amount of a compound effective for providing some degree of prevention of the progression of UC (i.e., provide protective effects), amelioration of the symptoms of UC, and amelioration of the reoccurrence of UC. The method involves administering an effective amount of a compound selected from the general formulae which are set forth hereinbefore. The present invention relates to a pharmaceutical composition incorporating a compound selected from the general formulae which are set forth hereinbefore. The compounds normally are not optically active. However, certain compounds can possess substituent groups of a character so that those compounds possess optical activity. Optically active compounds can be employed as racemic mixtures or as enantiomers. The compounds can be employed in a free base form or in a salt form (e.g., as pharmaceutically acceptable salts, such as chloride, perchlorate, astorbate, sulfate, tartrate, fumarate, citrate, malate, lactate or aspartate salts).

The pharmaceutical composition also can include various other components as additives or adjuncts. Exemplary pharmaceutically acceptable components or adjuncts include antioxidants, free radical scavenging agents, peptides, antibiotics, bacteriostatic agents, immunosuppressives, buffering agents, anti-inflammatory agents, anti-pyretics, analgesics, anti-diarrheal agents, membrane stabilizing agents, oils, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); as a suppository or an enema; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet (e.g., as is Asacol), a hard gelatin capsule (e.g., as is Dipentum) or as a rectal suspension enema (e.g., as is Rowasa). As another example, the compounds can be delivered transdermally using the types of patch technologies available from Ciba-Geigy Corporation and Alza Corporation. The administration of the pharmaceutical compositions of the present invention can be intermittent, or at a gradual, o continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with receptor sites within the body of the subject that effect the functioning within the gastrointestinal tract.

The dose of the compound is that amount effective to prevent occurrence of the symptoms of the disease or to treat some symptoms of the disease from which the patient suffers. By "effective amount", "therapeutic amount" or "effective dose" is meant that amount sufficient to elicit the desired pharmacological or therapeutic effects, thus resulting in effective prevention or treatment of the disease. Prevention of the disease is manifested by a prolonging or delaying of the onset of the symptoms of the disease. Treatment of the disease is manifested by a decrease in the symptoms associated with the disease or an amelioration of the reoccurrence of the symptoms of the disease.

The effective dose can vary, depending upon factors such as the condition of the patient, the severity of the symptoms of the disease, and the maimer in which the pharmaceutical composition is administered. For human patients, the effective dose of typical compounds generally requires administering the compound in an amount of at least about 1, often at least about 10, and frequently at least about 25 mg/24 hr./patient. For human patients, the effective dose of typical compounds requires administering the compound which generally does not exceed about 500, often does not exceed about 400, and frequently does not exceed about 300 mg/24hr./patient. In addition, administration of the effective dose is such that the concentration of the compound within the plasma of the patient normally does not exceed 500 ng/ml, and frequently does not exceed 100 ng/ml.

The compounds of the present invention have the ability to interact with certain nicotinic cholinergic receptors within the body of the patient. As such, these compounds have the ability to express nicotinic pharmacology. Relevant receptor sites can include high affinity sites characteristic of those found in the brain. The receptor binding constants of typical compounds useful in carrying the present invention generally are greater than 1 nM, often are greater than 200 nM, and frequently are greater than about 500 nM. The receptor binding constants of such typical compounds generally are less than 10 µM, often are less than about 7 gM, and frequently are less than about 2 µM. Receptor binding constants provide a measure of the ability of the compound to bind to half of the relevant receptor sites of certain cells of the patients. See, Cheng, et al., *Biochem. Pharmacol.* Vol. 22, pp. 3099–3108 (1973).

Dopamine release is associated with regulation of blood flow to the gastrointestinal tract. See, Goodman and Gilman's *The Pharmacological Basis of Therapeutics*, 16th Ed., pp. 138–175 (1980). Positive effects of nicotine on rectal blood flow have been implicated in the pathophysiology of UC. See, Srivastava et al., *Gut*, Vol. 31, pp. 1021–1024 (1990)). The compounds useful according to the method of the present invention have the ability to demonstrate a nicotinic function by effectively eliciting neurotransmitter secretion. In particular, such compounds have the ability to cause the release or secretion of dopamine. Generally, typical compounds useful in carrying the present invention provide for the secretion of dopamine in amounts of at least 25 percent, often at least 50 percent, and frequently at least 75 percent, of that elicited by an equal molar amount of (S)-(–)-nicotine. Certain compounds of the present invention can provide secretion of dopamine in an amount which can exceed that elicited by an equal molar amount of (S)-(–)-nicotine.

It has been proposed that there exists an interaction between nicotinic processes and the immune system. See, Lukas et al., *Intl. Rev. Neurobiol.*, Vol. 34, pp. 25–130 (1992) and Jonakait, *TINS*, Vol. 16 (10), pp. 419–423 (1993). For example, deafferentation of sympathetic ganglia (i.e., removal of nicotinic input) results in sensitization of non-neuronal cells within the ganglion and increased production of the sympathetic neuron differentiation factor LIF (Leukemia Inhibitory Factor). Such production is blocked by corticosteroids, which are known to improve symptoms of UC. The increase in LIF in turn results in an increase in Substance P and acetylcholine in the ganglion neurons, resulting in stimulation of an immune system reaction, thereby leading to an increase in interleukin-2 (IL-2), interleukin-1 (IL-1), interleukin-6 (IL-6) and TNF-a. See, Jonakait, *TINS*, Vol. 16 (10), pp. 419–423 (1993). One mechanism by which the compounds of the present invention may be beneficial towards preventing and/or treating UC involves the capability of those compounds to provide nicotinic cholinergic input required to inhibit the activation of LIF, thereby preventing (i) a subsequent series of immune system reactions, and (ii) the formation of IL-1, IL-2 and TNF-a.

The administration of nicotine has been shown to elicit positive effects upon memory and induce neurotransmitter release in the CNS, but also inhibit the production of IL-2. See, Denicoff et al., *Ann. Intern. Med.*, Vol. 107, pp. 293–300 (1987); Plata-Salaman et al., *Neurosc. Biobch. Res.*, Vol. 15, pp. 185–215 (1991) and Hanish et al., *J. Neurosc.*, Vol. 13, pp. 3368–3374 (1993). Thus, nicotinic compounds have been expected to exhibit an antagonistic effect between neurotransmitter release and IL-2 release. Thus, it is believed that compounds that express nicotinic pharmacology, as judged by binding to nicotinic receptors and modulation of neurotransmitter release, should provide the pharmacological capability to interrupt the cycle of immune response-mediated inflammatory symptoms of diseases such as UC.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations derived from muscle preparations. Thus, such compounds exhibit receptor activation constants (i.e., which provide a measure of the concentration of compound needed to activate half of the relevant receptor sites of the skeletal muscle of a patient) which are relatively high. Generally, typical compounds useful in carrying the present invention activate isotopic rubidium ion flux by less than 15 percent, often by less than 10 percent, and frequently by less than 5 percent, of that elicited by an equal molar amount of (S)-(–)-nicotine.

The compounds of the present invention, when employed in effective amounts in accordance with the method of the present invention, are selective to certain relevant nicotinic receptors, but do not cause significant activation of receptors associated with unwanted side effects. By this is meant that a particular dose of compound resulting in prevention and/or treatment of UC, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical compounds useful in carrying the present invention activate isotopic rubidium ion flux by less than 15 percent, often by less than 10 percent, and frequently by less than 5 percent, of that elicited by an equal molar amount of (S)-(–)-nicotine.

Compounds of the present invention, when employed in effective amounts in accordance with the method of the present invention, are effective towards providing some degree of prevention of the progression of UC, amelioration of the symptoms of UC, and amelioration of the reoccurrence of UC. However, such effective amounts of those compounds are not sufficient to elicit any appreciable side effects, as demonstrated by increased effects relating to the cardiovascular system, and effects to skeletal muscle. As such, administration of compounds of the present invention provides a therapeutic window in which treatment of UC is provided, and side effects are avoided. That is, an effective dose of a compound of the present invention is sufficient to provide the desired effects within the gastrointestinal tract, but is insufficient (i.e., is not at a high enough level) to provide undesirable side effects. Typically, effective administration of a compound of the present invention resulting in treatment of UC occurs upon administration of less than $\frac{1}{5}$, and often less than $\frac{1}{10}$, that amount sufficient to cause any side effects to a significant degree.

The following example is provided in order to further illustrate various embodiments of the invention but should not be construed as limiting the scope thereof. Unless otherwise noted, all parts and percentages are by weight.

EXAMPLE

Sample No. 1 is (E)-4-(5-pyrimidinyl)-3-butene-1-amine monofumarate (compound III monofumarate), which was prepared essentially in accordance with the following techniques.

N-3-Butene-1-phthalimide (I):

This compound was prepared essentially in accordance with the techniques described in Heck, et al., *J. Org. Chem.*, Vol. 43, pp. 2947–2949 (1978).

(E)-N-[4-(5-Pyrimidinyl)-3-butene-1-]phthalimide (II):

Under a nitrogen atmosphere, a mixture of I (28.20 g, 140 mmol), 5-bromopyrimidine (21.63 g, 136 mmol), palladium(II) acetate (306 mg, 1.4 mmol), tri-o-tolylphosphine (828 mg, 2.7 mmol), and trimethylamine (27.54 g, 272 mmol) was stirred and heated at ~110° C. for 27 h. The precipitated brown solids were slurried in water, filtered, and dissolved in hot N,N-dimethylformamide (DMF) (75 mL). Charcoal (Darco® G-60, 1 g) was added and the mixture filtered through Celite® (1.8 g), washing the filter cake with hot DMF (10 mL). The filtrate was diluted with an equal volume of water and cooled at 5° C. for 15 h. The solids were filtered, washed with water (2×25 mL) and dried, producing a beige, crystalline powder (28.55 g, 75.1%). Further purification, involving two recrystallizations from DMF-water (1:1), followed by two recrystallizations from toluene afforded compound II as a light beige, crystalline powder (18.94 g, 49.8%), mp 177°–178.5° C.

IR (KBr): 3445 (w), 3014 (w), 2951 (w), 1768 (m, C=O), 1703 (s, C=O), 1650 (w, C=C), 1558 (m), 1433 (s), 1402 (s), 1367 (s), 1330 (m), 1057 (m), 964 (m, trans C=C), 879 (m), 721 (s, 1,2-disubst. benzene), 717 (w, 5-pyrimidinyl), 633 (w, 5-pyrimidinyl)cm$^{-1}$.

$^1$H NMR(CDCl$_3$): δ 9.01 (s, 1H), 8.60(s, 2H), 7.85 (m, 2H), 7.70(m, 2H), 6.35 (m, 2H), 3.85 (m, 2H), 2.63 (m, 2H).

$^{13}$C NMR (CDCl$_3$): δ 168.26, 157.21, 154.09, 134.07, 131.97, 131.37, 130.69, 125.60, 123.33, 37.11, 32.49.

EI-MS: m/z (relative intensity) 279 (M$^+$, 5%), 160 (100%), 131 (43%), 119 (45%), 104 (17%), 77 (31%), 65 (13%), 51 (11%).

HRMS: Calcd. for C$_{16}$H$_{13}$N$_3$O$_2$ (M$^+$): m/z 279.0992. Found: 279.1008.

Anal. Calcd. for C$_{16}$H$_{13}$N$_3$O$_2$: C, 68.81; H, 4.69; N, 15.05. Found: C, 68.68; H, 4.82; N, 14.94.

(E)-4-(5-Pyrimidinyl)-3-butene-1-amine (III):

Hydrazine hydrate (2.69 g, 53.7 mmol, 99%) was added to a mixture of II (6.00 g, 21.5 mmol) and methanol (100 mL), and the mixture was stirred at ambient temperature for 27 h. The white suspension was diluted with 1M NaOH solution (400 mL) and extracted with chloroform (5×100 mL). The chloroform extracts were combined, dried (Na$_2$SO$_4$), filtered, and concentrated by rotary evaporation. The residue was vacuum dried 5 h at 55° C. to give (E)-4-(5-pyrimidinyl)-3-butene-1-amine (III) as a light yellow oil (2.95 g, 92.2 %), which was used without further purification.

IR (film): 3345 (br, N—H), 1655 (m, C=C), 1560 (s), 1490 (s), 1440 (s), 1415 (s), 1390 (m), 1317 (s), 1190 (m), 968 (m, trans C=C), 721 (s, 5-pyrimidinyl), 636 (m, 5-pyrimidinyl) cm$^{-1}$.

$^1$H NMR (CDCl$_3$): δ 9.13 (s, 1H), 8.68 (s, 2H), 6.38 (m, 2H), 2.84 (t, 2H, J=7 Hz), 2.40 (m, 2H), 1.26 (br s, 2H).

$^{13}$C NMR (CDCl$_3$): δ 157.04, 153.96, 133.16, 130.92, 124.82, 41.36, 37.44.

EI-MS: m/z (relative intensity) 148 (M$^+$−1, 0.1%), 132 (1%), 120 (100%), 93 (31%), 66 (40%), 51 (11%), 44 (14%).

The monofumarate of III was prepared by adding a warm solution of fumaric acid (156 mg, 1.34 mmol) in ethanol (5 mL) to a warm solution of III (100 mg, 0.67 mmol) in ethanol (3 mL). The mixture was concentrated by rotary evaporation, and the slightly yellow solids were recrystallized from ethanol-ether (1:1). The solids were filtered, washed with ethanol, ether, and vacuum dried at 50° C. for 24 h, affording the monofumarate as a white, crystalline powder (63.8 mg, 35.9%), mp 160°–161.5° C.

IR (KBr): 3300–2300 (br, s, amine-carboxylate), 1705 (s, C=O), 1664 (s), 1606 (s, C=C), 1556 (s), 1409 (s, fumarate), 1254 (m), 1186 (m), 981 (m, trans C=C), 852 (m), 796 (m), 723 (w, 5-pyrimidinyl), 648 (m, fumarate), 631 (m, 5-pyrimidinyl) cm$^{-1}$.

$^1$H NMR (D$_2$O): δ 9.00 (s, 1H), 8.84 (s, 2H), 6.69 (s, 2H), 6.63 (d, 1H, J=16.4 Hz), 6.52 and 6.46, (dt, 1H, J=16.1, 6.8 Hz), 3.20 (m, 2H), 2.72 (m, 2H).

$^{13}$C NMR (D$_2$O): δ 171.45, 154.10, 134.63, 131.04, 130.23, 126.05, 38.40, 30.33.

Anal. Calcd. for C$_8$H$_{11}$N$_3$·C$_4$H$_4$O$_4$: C, 54.33; H, 5.70; N, 15.84. Found: C, 54.24; H, 5.75; N, 15.65.

Sample No. 2 is (E)-N-methyl-4-(5-pyrimidinyl)-3-butene-1-amine (compound VI), which was prepared essentially in accordance with the following techniques.

(E)-N-tert-Butyloxycarbonyl-4-(5-pyrimidinyl)-3-butene-1-amine (IV):

A solution of di-tert-butyl dicarbonate (2.66 g, 12.2 mmol) in methylene chloride (10 mL) was added dropwise over 5 min to a stirring solution of (E)-4-(5-pyrimidinyl)-3-butene-1amine (III) (1.70 g, 11.4 mmol) in methylene chloride at 0° C. The yellow solution was stirred at 0° C. for 15 min and at ambient temperature for 22 h. Concentration by rotary evaporation, followed by vacuum drying at 30° C. for 15 h afforded a yellow oil. The oil was chromatographed on silica gel (165 g), eluting first with ethyl acetate to remove impurities. Elution with chloroform-methanol (2:1) afforded the product which was re-chromatographed eluting with ethyl acetate. Selected fractions were combined in chloroform and concentrated by rotary evaporation. The residue was vacuum dried at 35° C. for 48 h to give compound IV as a light yellow oil (2.56 g, 90.1%), which crystallized upon cooling, affording a light yellow, crystalline solid, mp 54°–55.5° C.

IR (KBr): 3030 (w), 2990 (w), 2980 (w), 2965 (w), 2935 (w), 3298 (s, amide N—H), 1712 (s, carbamate C=O), 1657 (w, C=C), 1560 (s), 1535 (s, amide N—H), 1433 (s), 1414 (s), 1367 (s, tert-butyl), 1275 (s, amide N—H), 1246 (s, ester C=O), 1174 (s, ester C=O), 1149 (s), 1111 (m), 987 (m), 966 (m trans C=C), 723 (w, 5-pyrimidinyl), 636 (m, 5-pyrimidinyl) cm$^{-1}$.

$^1$H NMR (CDCl$_3$): δ 9.05 (s, 1H), 8.70 (s, 2H), 6.37 (m, 2H), 4.59 (br s, 1H), 3.30 (m, 2H), 2.43 (m, 2H), 1.46 (s, 9H).

$^{13}$C NMR(CDCl$_3$): δ 157.34, 156.83, 155.84, 154.18, 153.79, 132.24, 130.75, 125.15, 79.42, 39.64, 34.05, 28.56, 28.20.

EI-MS: m/z (relative intensity) 249 (M$^+$, 0.1%), 193 (15%), 176 (24%), 132 (16%), 120 (79%), 119 (85%), 93 (19%), 65 (24%), 57 (100%).

Anal. Calcd. for C$_{13}$H$_{19}$N$_3$O$_2$: C, 62.62; H, 7.68; N, 16.86. Found: C, 62.61; H, 7.62; N, 16.78.

(E)-N-Methyl-N-tert-Butyloxycarbonyl-4-(5-pyrimidinyl)-3-butene-1-amine (V):

Under a nitrogen atmosphere, sodium hydride (0.78 g, 19.5 mmol, 60% dispersion in oil) was added to a stirring solution of IV (0.50 g, 2.0 mmol), 1,2-dimethoxyethane (20 mL), DMF (25 mL), and a trace of diisopropylamine. The mixture was stirred at ambient temperature for 45 min, and a solution of iodomethane (2.59 g, 18.3 mmol) in 1,2-dimethoxyethane (5 mL) was added. The mixture was stirred at ambient temperature for 3 days, cooled, and water (25 mL) was added dropwise. The mixture was diluted with water (200 mL) and extracted with chloroform (7×50 mL). All chloroform extracts were combined, dried (Na$_2$SO$_4$), filtered, and concentrated by rotary evaporation. The residue was dried under high vacuum at ambient temperature to give a red-brown oil. The oil was chromatographed on silica gel (50 g), eluting with ethyl acetate. Selected fractions were combined, concentrated by rotary evaporation, and dried under high vacuum at ambient temperature to give compound V as a light yellow oil (0.40 g, 76.1%).

IR (film): 3650–3200 (br, w), 2980 (m), 2940 (m), 1697 (s, carbamate C=O), 1556 (s), 1484 (s), 1452 (s), 1420 (s, N—CH$_3$), 1411 (s, tert-butyl), 1394 (s, tert-butyl), 1369 (s), 1304 (m), 1249 (m, ester C=O), 1218 (m), 1163 (s, ester C—O), 1136 (s), 972 (m, trans C=C), 883 (m), 774 (m), 721 (m, 5-pyrimidinyl), 631 (m, 5-pyrimidinyl) cm$^{-1}$.

$^1$H NMR (CDCl$_3$): δ 9.01 (s, 1H), 8.63 (s, 2H), 6.31 (m, 2H), 3.32 (m, 2H), 2.82 (s, 3H), 2.44 (m, 2H), 1.39 (s, 9H).

$^{13}$C NMR(CDCl$_3$): δ 157.06, 155.70, 153.95, 132.49, 130.94, 124.73, 79.51, 34.38, 28.45.

EI-MS: m/z (relative intensity) 263 (M$^+$, 0.3%), 207 (5%), 190 (7%), 144 (24%), 133 (9%), 120 (39%), 93 (13%), 88 (15%), 65 (11%), 57 (100%), 44 (89%).

HRMS: Calcd. for C$_{14}$H$_{21}$N$_3$O$_2$ (M$^+$): m/z 263.1634. Found: 263.1643.

(E)-N-Methyl-4-(5-pyrimidinyl)-3-butene-1-amine (VI):

Under a nitrogen atmosphere, iodotrimethylsilane (0.50 g, 2.5 mmol) was added dropwise, at ambient temperature, to a stirring solution of V (0.33 g, 1.2 mmol) in chloroform (20 mL). The red-brown mixture was stirred 30 min and methanol (20 mL) was added. The mixture was stirred 1 h and concentrated by rotary evaporation. The residue was basified with 1M NaOH solution (25 mL) and extracted with chloroform (7×25 mL). The chloroform extracts were combined, dried (Na$_2$SO$_4$) and concentrated by rotary evaporation, affording a brown oil. The oil was chromatographed on silica gel (35 g), eluting with methanol-ammonium hydroxide (10:1). Selected fractions were combined, vacuum dried at 45° C. for 3 h, affording (E)-N-methyl-N-4-(5-pyrimidinyl)-3-butene-1-amine (VI) as a brownish-yellow oil (0.12 g, 59.6%).

IR (film): 3148 (br, s, N—H), 1653 (s, C=C), 1560 (s), 1473 (m), 1435 (s), 1414 (s, N—CH$_3$), 970 (m, trans C=C), 721 (s, 5-pyrimidinyl), 636 (s, 5-pyrimidinyl) cm$^{-1}$.

$^1$H NMR (CDCl$_3$): δ 9.02 (s, 1H), 8.68 (s, 2H), 6.37 (m, 2H), 2.76 (t, 2H, J=6.8 Hz), 2.46 (m, 5H, including a N—CH$_3$ singlet), 1.65 (br s, 1H).

$^{13}$C NMR (CDCl$_3$): δ 157.09, 154.01, 132.99, 130.90, 124.81, 50.76, 36.06, 33.35.

EI-MS: m/z (relative intensity) 146 (0.3%), 132 (0.4%), 120 (22%), 93 (4%), 65 (4%), 44 (100%).

HRMS: Calcd. for C$_7$H$_8$N$_2$ (M$^+$–44): m/z 120.0676. Found: 120.0687.

Sample No. 3 is (E)-4-[3-(5-methoxypyridin)yl]-3-butene-1-amine monofumarate (compound IX monofumarate), which was prepared essentially in accordance with the following techniques.

3-Bromo-5-methoxypyridine (VII)

This compound was prepared essentially in accordance with the techniques described in Comins et al., J. Org. Chem., Vol. 55, pp. 69–73 (1990)

(E)-N-4-[3-(5-methoxypyridin)yl]-3-butene-1-phthalimide (VIII):

Under a nitrogen atmosphere, a mixture of N-3-butene-1-phthalimide (I) (5.51 g, 27.4 mmol), 3-bromo-5-methoxypyridine (VII) (5.00 g, 26.6 mmol), palladium(II) acetate (59.7 mg, 0.27 mmol), tri-o-tolylphosphine (162 mg, 0.53 mmol), and triethylamine (5.38 g, 53.2 mmol) was stirred and heated at ~100° C. for 21 h. The precipitated brown solids were slurried in water, filtered, and dissolved in hot DMF (30 mL). The mixture was filtered through Celite® (1 g), washing the filter cake with hot DMF (10 mL). The filtrate was diluted with an equal volume of water and cooled at 5° C. for 15 h. The solids were filtered, washed with water (2×10 mL), cold ethanol (10 mL), and dried, producing a beige, crystalline powder (7.79 g, 95.0%). Further purification, involving two recrystallizations from DMF-water (1:1) afforded compound VIII as a light beige, crystalline powder (5.36 g, 65.4%), mp 148°–151° C. An analytical sample was recrystallized from toluene, affording a light beige, crystalline powder, mp 148°–151.5° C.

IR (KBr): 3440 (w), 3040 (m), 2960 (s), 2940 (s), 2825 (w), 1766 (m, C=O), 1700 (s, C=O), 1654 (m, C=C), 1580 (m, pyridinyl), 1455 (s), 1420 (s), 1320 (m), 1190 (m), 1000 (s), 973 (s, trans C=C), 867 (s, 3,5-disubst. pyridine), 723 (s, 1,2-disubst. benzene), 703 (s, 3,5-disubst. pyridine) cm$^{-1}$.

$^1$H NMR (CDCl$_3$): δ 8.14 (s, 1H), 8.08 (s, 1H), 7.82 (m, 2H), 7.69 (m, 2H), 7.10 (dd, 1H, J=2.4, 2.0 Hz), 6.38 (d, 1H, J=16.1 Hz), 6.25 and 6.20 (dt, 1H, J=15.9, 6.8 Hz), 3.84 (t, 5H, including an O—CH$_3$ singlet, J=7.1 Hz), 2.62 (dq, 2H, J=7.1, 1.0 Hz).

$^{13}$C NMR (CDCl$_3$): δ0 168.27, 155.73, 140.72, 136.45, 133.96, 132.05, 129.00, 123.26, 116.80, 55.52, 37.34, 32.30.

EI-MS: m/z (relative intensity) 308 (M$^+$, 13%), 160 (100%), 148 (8%), 133 (10%), 105(8%), 77 (15%).

Anal. Calcd. for C$_{18}$H$_{16}$N$_2$O$_3$: C, 70.12; H, 5.23; N, 9.09. Found: C, 70.34; H, 5.29; N, 9.00.

(E)-4-[3-(5-methoxypyridin)yl]-3-butene-1-amine (IX):

Hydrazine hydrate (245 mg, 4.90 mmol, 99%) was added to a mixture of VIII (500 mg, 1.62 mmol) and methanol (20 mL), and the mixture was stirred at ambient temperature for 20 h. The gray suspension was diluted with 1M NaOH solution (190 mL) and extracted with chloroform (5×25 mL). The chloroform extracts were combined, dried (Na$_2$SO$_4$), filtered, and concentrated by rotary evaporation. The crude product (287 mg) was further purified by vacuum distillation, affording compound IX (183 mg, 62.3%) as a light yellow oil, bp 110° C. at 0.05 mmHg.

IR (film): 3350 (br, s), 3035 (s), 2940 (s), 2840 (m), 1585 (s), 1460 (s), 1425 (s), 1320 (s), 1295 (s, ArO—CH$_3$), 1185

(m), 1160 (m), 1050 (m), 1020 (sh), 965 (s, trans C=C), 885 (m, 3,5-disubst. pyridine), 820 (w), 7 10 (m, 3,5-disubst. pyridine).

$^1$H NMR (CDCl$_3$): δ 8.16 (d, 1H, J=2.0 Hz), 8.13 (d, 1H, J=2.9 Hz), 7.14 (dd, 1H, J=2.6, 2.0 Hz), 6.41 (d, 1H, J=15.9 Hz), 6.27 and 6.22 (dt, 1H, J=15.9, 7.1 Hz), 3.84 (s, 3H), 2.84 (t, 2H, J=6.6 Hz), 2.36 (dq, 2H, J=6.6, 1.0 Hz).

$^{13}$C NMR (CDCl$_3$): 155.79, 140.70, 136.24, 133.72, 130.79, 128.27, 116.91, 55.57, 37.29, 29.70.

EI-MS: m/z (relative intensity) 178 (M$^+$, 0.4%), 149 (88%), 148 (100%), 133 (12%), 105 (9%), 78 (10%).

The monofumarate of IX was prepared by adding a warm solution of fumaric acid (131 mg, 1.12 mmol) in 2-propanol (15 mL) to compound IX (166 mg, 0.93 mmol). After stirring 30 min, the solution was concentrated by rotary evaporation to a white powder. The crude product was recrystallized from 2-propanol, and the mixture was stored at ambient temperature o for 15 h. The solids were filtered, washed with cold 2-propanol, ether, and vacuum dried at 50° C. for 6 h, affording the monofumarate as a white, crystalline powder (177 mg, 64.6%), mp 151°–153° C.

IR (KBr): 3300–2400 (br, s, amine-carboxylate), 1700 (s, C=O), 1630 (s, C=O), 1570 (sh), 1535 (m), 1460 (m), 1435 (m), 1290 (s, ArO—CH$_3$), 1158 (m), 1040 (m), 982 (s, trans C=C), 875 (m, 3,5-disubst. pyridine), 793 (m), 705 (m, 3,5-disubst. pyridine), 652 (m).

$^1$H NMR (D$_2$O): δ 8.31 (s, 1H), 8.25 (s, 1H), 7.85 (s, 1H), 6.68 (d, 1H, J=16.1Hz) 6.57 (s, 2H), 6.53 and 6.48 (dt, 1H, J=15.9, 7.1 Hz), 3.98 (s, 3H), 3.21 (t, 2H, J=7.1 Hz), 2.68 (q, 2H, J=7.1 Hz).

$^{13}$C NMR(D$_2$O): δ 172.93, 156.77, 136.17, 135.62, 134.90, 131.81, 130.25, 128.04, 122.44, 56.31, 38.54, 30.14.

Anal. Calcd. for C$_{10}$H$_{14}$N$_2$O·C$_4$H$_4$O$_4$: C, 57.14; H, 6.16; N, 9.52. Found: C, 56.91; H, 6.18; N, 9.51.

Sample No. 4 is N-Methyl-4-(3-pyridinyl)-3-butyne-1-amine which was prepared essentially in accordance with the following techniques.

1,1-Dibromo-2-(3-pyridinyl)-ethylene (X)

Tetrabromomethane (24.82 g, 0.747 mole) and triphenylphosphine (39.17 g, 0.149 mole) were stirred together in dry methylene chloride (100 mL) for 5 min. at 0° C. under a nitrogen atmosphere. To this mixture was added dropwise pyridine 3-carboxaldehyde (4 g, 0.0373 mole). The solution was then stirred for 45 min. at ambient temperature. The reaction mixture was extracted with aqueous 6N hydrochloric acid (3×25 mL), the aqueous layer basified with solid sodium bicarbonate to pH 8–9 and extracted with chloroform (4×25 mL). The combined organic liquours were dried over anhydrous sodium sulfate, filtered and concentrated on a rotary evaporator to give a dark colored syrup. The crude product was chromatographed on silica gel (70–230 mesh) with chloroform:methanol (95:5) as eluant, to afford a light yellow solid (5.0 g, 70%) which rapidly turned dark on standing.

$^1$H NMR(CDCl$_3$) δ 8.65 (s, 1H), 8.58 (d, 1H), 8.00 (d, 1H), 7.45 (s, 1H), 7.22–7.36 (m, 1H).

Anal. calcd. for C$_7$H$_4$NBr$_2$: C, 31.94; H, 1.90; N, 5.32; Br, 60.84. Found: C, 32.11; H, 2.03; N, 5.50; Br, 60.99.

4-(3-Pyridinyl)-3-butyne-1-ol (XI)

To dry THF (10 mL) combined in a 50 mL round-bottomed flask fixed with a nitrogen gas balloon was added X (2.5 g, 0.01 mole). The flask was cooled to −78° C. in an acetone-dry ice bath, and n-butyl lithium in THF (22 mL of a 2.5 molar solution in THF) was added dropwise via a syring during constant stirring. After addition, the solution was stirred for 1 hour. The reaction mixture temperature was then adjusted to −60° C. and ethylene oxide (1 mL) was added in one portion, and the reaction was allowed to warm to ambient temperature with stirring. The resulting reaction mixture was quenched with water (10 mL) and extracted with chloroform (3×25 mL), the combined organic liquors dried over anhydrous sodium sulfate, filtered and concentrated on a rotary evaporator under reduced pressure. The resulting oil was chromatographed on silica gel to afford the product as a light brown liquid (590 mg, 40%).

$^1$H NMR (CDCl$_3$) δ 8.71 (s, 1H), 8.49 (d, 1H), 7.68 (d, 1H) 7.29–7.36 (m, 1H), 3.92 (t, 2H), 2.80 (m, 2H).

Anal. calcd. for C$_9$H$_9$NO: C, 73.46; H, 6.12; N, 9.52. Found: C, 73.61; H, 6.31; N, 9.66.

Methanesulfonate ester of 4-(3-Pyridinyl)-3-butyne-1-ol (XII)

In dry methylene chloride (2 mL) was dissolved XI (0.15 g, 1.0 mmole), and to this solution was added triethylamine (0.184 ml, 1.3 mmole). The reaction was stirred overnight under nitrogen atmosphere. The mixture was cooled to 4° C. and methane sulfonyl chloride (0.15 g, 1.3 mmole) was added. The reaction mixture was then poured over ice/water (10 mL) and the resulting mixture stirred for 5 min. To this mixture was added saturated aqueous sodium bicarbonate solution (5 mL) chilled to 4° C., and the mixture stirred for 30 min., then extracted with chloroform (4×10 mL). The combined organic fractions were dried over anhydrous sodium sulfate, filtered and the volume concentrated on a rotary evaporator. The product was further purified using gel chromatography, eluting with a chloroform: methanol mixture containing 1% triethylamine. Yield of XII is 0.218 g (about 97%).

$^1$H NMR (CDCl$_3$) δ 8.59 (s, 1H), 7.62 (d, 1H), 7.18–7.22 (m, 1H), 4.31 (t, 2H), 3.00 (s, 3H), 2.80 (t, 2H).

N-Methyl-4-(3-pyridinyl)-3-butyne-1-amine (XIII)

An aqueous methylamine solution (5mL, 40%, 58.7 mmole) was mixed with XII (200 mg, 0.08 mmole) and stirred for 3 hr. in a sealed tube at 45° C. After the reaction was complete, water (10 mL) was added to the cooled reaction mixture, and the reaction mixture was extracted with chloroform (10×5 mL). The combined organic extracts were dried over anhydrous sodium sulfate, filtered and concentrated. The residue obtained was chromatographed on a silica gel column using methanol:chloroform (1:9) and then with a chloroform: methanol mixture containing 1% triethylamine as eluent. About 70 mg of XIII was obtained as a slightly yellow syrup, which was distilled at 110°–112° C., 0.04 mm Hg. XIII was converted to its mono fumarate salt form, which exhibits a melting point of 103°–104° C.

Free base. $^1$H NMR (CDCl$_3$) δ 8.61 (s, 1H), 8.48 (d, 1H), 7.62 (d, 1H), 7.20 (t, 1H), 2.82 (t, 2H), 2.61 (t, 2H), 2.33 (s, 3H), 1.4 (br s, 1H).

Fumarate salt. $^1$H NMR (D$_2$O) δ 8.51 (S, 1H), 8.39 (d, 1H), 7.91 (d, 1H), 7.40 (m, 1H), 6.28 (s, 2H), 3.20 (t, 2H), 2.80 (t, 2H), 2.62 (s, 3H).

$^{13}$C NMR (D$_2$O ) δ 164.5, 151.8, 148.0, 146.0, 138.8, 128.2, 124.5, 93.0, 82.3, 50.4, 36.2, 20.1.

Anal. calcd. for C$_{14}$H$_{16}$N$_2$O$_4$: C, 60.86; H, 5.70; N, 10.14. Found: C, 60.84; H, 5.72; N, 10.23.

Sample No. 5 is (Z)-metanicotine which was prepared essentially in accordance with the following techniques.

(Z)-Metanicotine (XIV)

Into a hydrogenation bottle together with methanol (20 mL), glacial acetic acid (1 mL) and a catalytic amount of quinoline was placed XIII free base (200 mg, 1.25 mmole). Lindlar's catalyst (palladium/calcium carbonate poisoned with lead) (60 mg) was added and the mixture hydrogenated at 50 psig in a Parr reaction apparatus overnight at ambient temperature. The catalyst was filtered off, the resulting solution basified with aqueous sodium hydroxide (50% w/v) to a pH 8–9, and then extracted with chloroform (3×25 mL). The combined organic liquors were concentrated on a rotary evaporator, and the residue chromatographed on 60–230 mesh silica gel, using chloroform:methanol:triethylamine (90:10: 1) as eluent, to afford XIV as a colorless oil at about 100% yield. XIV is converted to its difumarate salt, which has a melting point of 117°–118° C.

Free-base, $^1$H NMR (CDCl$_3$) δ 8.56 (s, 1H), 8.42 (d, 1H), 7.60 (d, 1H), 7.22 (m, 1H), 6.81 (m, 1H), 6.51 (d, 1H), 2.79 (t, 2H), 2.52 (m, 2H), 2.41 (s, 3H).

Difumarate salt. $^1$H NMR (D$_2$O) δ 8.48 (br s, 2H), 8.10 (d, 1H), 7.75–7.63 (m, 1H), 6.52 (d, 1H), 6.40 (s, 1H), 5.85–5.78 (m, 1H), 3.00 (t, 2H), 2.51 (m, 5H).

Anal. calcd. for C$_{10}$H$_{14}$N$_2$.2C$_4$H$_4$O$_4$: C, 54.82; H, 5.58; N, 7.10. Found: C, 54.47; H, 5.68; N, 6.98.

Sample No. 6 is (E)-N-methyl-4-[3-(6-methylpyridin)yl]-3-butene-1-amine which was prepared essentially in accordance with the following techniques.

6-Methylmyosmine (XV)

Sodium hydride (60% in oil) (1.9 g, 0.079 mole) was placed in a 250 mL two-necked round bottom flask and washed with dry THF (50 mL). A further aliquot of dry THF (100 mL) was added followed by a solution of N-vinylpyrrolidone (4.7 g, 0.04 mole) in dry THF (30 mL), and the mixture stirred for 30 min. at ambient temperature. A solution of ethyl 6-methylnicotinate (5.0 g, 0.033 mole) in dry THF (20 mL) was then added dropwise over 10 min., during which time evolution of hydrogen occurred. The reaction was flushed with nitrogen, and the mixture refluxed for 6 hr. After cooling, aqueous hydrochloric acid (6N, 25 mL) was added and the THF removed by rotory evaporation under reduced pressure. A further volume of aqueous hydrochloric acid (6N, 20 mL) was added and the mixture refluxed overnight. On cooling, the mixture was basified with aqueous sodium hydroxide (50% w/v) to pH 8–9, and XV was extracted with chloroform (5×20 mL). The combined organic liquours were dried over anhydrous sodium sulfate, filtered and the solvent evaporated to afford XV, which was crystallized from methanol as a tan solid (4.45 g, 84%).

$^1$H NMR (CDCl$_3$); δ 8.82 (s, 1H), 8.15 (d, 1H), 7.20 (d, 1H), 4.12 (t, 2H), 2.98 (t, 2H), 2.80 (s, 3H), 2.00 (m, 2H).

$^{13}$C NMR (CDCl$_3$) δ 172.5, 160.08, 148.1, 135.01, 122.7, 61.5, 34.8, 24.2, 22.2.

Anal. calcd. for C$_{10}$H$_{12}$N$_2$: C, 75.00, H, 7.50; N, 17.50. Found: C, 74.94; H, 7.51; N, 17.47.

(+/−)-6-Methylnornicotine (XVI)

Into a round bottom flask was placed XV (3.0 g, 0.018 mole), methanol (20 mL) and glacial acetic acid (4 mL). The mixture was cooled to −78° C. in a dry ice-acetone bath, and sodium borohydride (1.332 g, 0.36 mole) was added over 30 min. After addition, the reaction mixture was allowed to warm to ambient temperature, and stirred for 1 hr. The methanol then was removed on a rotary evaporator under reduced pressure and the residue was basified with aqueous sodium hydroxide (50% w/v) to pH 8–9. The aqueous solution was extracted with chloroform (5×25 mL) and the combined organic liquors dried over anhydrous sodium sulfate, filtered and evaporated on a rotary evaporator to afford XVI as a dark brown liquid, which was distilled at 4 mm Hg to yield a clear, colorless liquid (b.p. is 113°–114° C., 4mm Hg) (2.43 g, 80%).

$^1$H NMR (CDCl$_3$) δ 8.42 (s, 1H), 7.60 (d, 1H), 7.10 (d, 1H), 4.15 (t, 1H), 3.12 (m, 1H), 3.00 (m, 1H), 2.30 (s, 3H), 2.20–2.00 (m, 2H), 2.00–1.98 (m, 2H), 1.78–1.60 (m, 1H).

HClO$_4$ salt $^1$H NMR (D$_2$O) δ 8.62 (s, 1H), 8.40 (d, 1H), 7.81 (d, 1H), 3.58 (t, 2H), 2.78 (s, 3H), 2.40–2.20 (m, 4H).

Anal. calcd. for C$_{10}$H$_{16}$N$_2$Cl$_2$O$_8$: C, 33.05; H, 4.40; N, 7.71; Cl, 19.55. Found: C, 33.16; H, 4.46; N, 7.64; Cl, 19.43.

(+/−)-6-Methylnicotine (XVII)

Into a round bottom flask was placed XVI (2.0 g), and formaldehyde (37% w/v in water, 20 mL) and formic acid (95–97 % w/v, 45 mL), both at 0° C., were added. The mixture then was refluxed under nitrogen for 8 hr. The cooled reaction mixture was basified with aqueous sodium hydroxide (50% w/v) to pH 8–9, and the solution extracted with chloroform (5×25 mL). The combined organic liquors were dried over anhydrous sodium sulfate, filtered and evaporated; and the resulting oil distilled under reduced pressure to afford XVII as a clear odorless oil (b.p. 107° C. at 3 mm Hg, 92% yield).

$^1$H NMR (CDCl$_3$) δ 8.40 (s, 1H), 7.60 (d, 1H), 7.12 (d, 1H), 3.15 (t, 1H), 3.00 (t, 1H), 2.56 (s, 3H), 2.40–2.20 (m, 1H), 2.18–2.08 (m, 4H), 2.00–1.92 (m, 1H), 1.80–1.60 (m, 2H).

HClO$_4$ salt. Anal. calcd. for C$_{11}$H$_{18}$N$_2$Cl$_2$O$_8$: C, 35.01; H, 4.77; N, 7.42; Cl, 18.83. Found: C, 35.12; H, 4.85; N, 7.37; Cl, 18.76.

N-Ethylcarbamate of (+/−)-6-methylmetanicotine (XVIII)

To a stirred solution of XVII (3.0 g, 0.017 mole) in methylene chloride (25 mL) under nitrogen atmosphere was added dropwise a solution of ethylchloroformate (2.40 g) in methylene chloride (10 mL) at ambient temperature. The mixture was refluxed for 4 hr. After evaporation of solvent on a rotary evaporator under reduced pressure, the resulting oil was vacuum distilled to give XVIII as a thick viscous liquid (b.p. 172°–175° C., 4 mm Hg), which was further purified by silica column chromatography, to yield about 3 g of XVIII (70% yield).

$^1$H NMR (CDCl$_3$) δ 8.40 (s, 1H), 7.61 (d, 1H), 7.08 (d, 1H), 6.60 (d, 1H), 6.08–6.00 (m, 1H), 4.18 (q, 2H), 3.40 (m, 2H), 2.91 (s, 3H), 2.60–2.42 (m, 5H), 1.22 (t, 3H).

(E)-N-methyl-4-[3-(6-methylpyridin)yl]-3-butene-1-amine (XIX)

Into a round bottom flask was placed XVIII (3.0 g, 0.012 mole), and concentrated hydrochloric acid ( 15 mL) was added. The mixture was refluxed overnight, and the resulting solution basified with aqueous sodium hydroxide (50% w/v) to pH 8–9. The solution was extracted with chloroform (4×25 mL), the combined organic liquors dried over anhydrous sodium carbonate, filtered, and the solvent evaporated to afford an oil. Vacuum distillation of the oil afforded XIX as a clear, colorless liquid (b.p. 80° C. at 0.2 mm Hg, 78% yield). XIX then was provided in the form of a difumarate salt, m.p. 134°–135° C.

Difumarate salt. $^1$H NMR (DMSO-d$_6$) δ 8.42 (s, 1H), 7.76 (d, 1H), 7.20 (d, 1H), 6.52–6.24 (m, 4H), 3.00 (t, 2H), 2.60–2.00 (m, 6H).

Anal. Calcd. for C$_{11}$H$_{16}$N$_2$.2C$_4$H$_4$O$_4$: C, 55.88; H, 5.88; N, 6.86. Found: C, 55.72; H, 5.93; N, 6.83.

Sample No. 7 is N-methyl-(3-pyridinyl)-butane-1-amine, which was prepared essentially in accordance with the following techniques.

(E)-Metanicotine (0.4 g, 2.46 mmole) was dissolved in a mixture of methanol (20 mL) and glacial acetic acid (1 mL) and 5% Pd-C catalyst (30 mg) was added. The mixture was hydrogenated at 50 psig hydrogen for 2 hr. The reaction mixture then was filtered and the solvent removed on a rotary evaporator. To the residue was added water (5 mL) and the aqueous solution basified to pH 8–9 with 40% aqueous sodium hydroxide. The mixture then was extracted with chloroform (5×10 mL), and the combined organic liquors dried over potassium carbonate, filtered and solvent was evaporated under reduced pressure on a rotovaporator.

The resulting oil then was provided in the form of a difumarate salt, melting point being 115°–116° C.

Free base. $^1$H NMR (CDCl$_3$) δ 8.42 (m, 2H), 7.50 (d, 1H), 7.20 (m, 1H), 2.64–2.58 (m, 4H), 2.40 (s, 3H), 2.78–2.60 (m, 2H), 2.42–2.59 (m, 2H), 1.22 (broad s, 1H).

Difumarate salt. $^1$H NMR (D$_2$O) δ 8.64 (d, 2H), 8.43 (d, 1H), 8.00 (m, 1H), 6.62 (s, 4H), 3.24 (t, 2H), 2.90 (t, 2H), 2.70 (s, 3H), 1.81–1.69 (m, 4H).

Anal. calcd. for C$_{10}$H$_{16}$N$_2$·2C$_4$H$_4$O$_4$·1/2H$_2$O: C, 53.33; H, 6.17; N, 6.91. Found: C, 53.33; H, 6.06; N, 7.07.

Sample No. 8 is (E)-metanicotine which was provided generally using the techniques set forth by Laforge, *J.A.C.S.*, Vol. 50, p. 2477 (1928).

For comparison purposes, Sample No. C—I was provided. This sample is (S)-(–)-nicotine, which has been reported to have demonstrated a positive effect towards the treatment of various CNS disorders.

Determination of binding of compounds to relevant receptor sites

Rats (Sprague-Dawley) were maintained on a 12 hour light/dark cycle and were allowed free access to water and food supplied by Wayne Lab Blox, Madison, Wis. Animals used in the present studies weighed 200 to 250 g. Brain membrane preparations were obtained from brain tissue of either males or females.

Rats were killed by decapitation following anesthesia with 70% CO$_2$. Brains were removed and placed on an ice-cold platform. The cerebellum was removed and the remaining tissue was placed in 10 volumes (weight:volume) of ice-cold buffer (Krebs-Ringers HEPES: NaCl, 118 mM; KCl, 4.8 mM; CaCl$_2$, 2.5 mM; MgSO$_4$, 1.2 mM; HEPES, 20 mM; pH to 7.5 with NaOH) and homogenized with a glass-Teflon tissue grinder. The resulting homogenate was centrifuged at 18,000×g for 20 min. and the resulting pellet was resuspended in 20 volumes of water. After 60 min. incubation at 4° C., a new pellet was collected by centrifugation at 18,000×g for 20 min. After resuspension in 10 volumes of buffer, a new final pellet was again collected by centrifugation at 18,000×g for 20 min. Prior to each centrifugation step, the suspension was incubated at 37 ° C. for 5 min. to promote hydrolysis of endogenous acetylcholine. The final pellet was overlayered with buffer and stored at –70 ° C. On the day of the assay, that pellet was thawed, resuspended in buffer and centrifuged at 18,000×g for 20 min. The pellet obtained was resuspended in buffer to a final concentration of approximately 5 mg protein/ml. Protein was determined by the method of Lowry et al., *J. Biol. Chem.*, Vol. 193, pp. 265–275 (1951), using bovine serum albumin as the standard.

The binding of L-[$^3$H]nicotine was measured using a modification of the method of Romano et al., *Science*, Vol. 210, pp. 647–650 (1980) as described previously by Marks et al., *Mol. Pharmacol.*, Vol. 30, pp. 427–436 (1986). The L-[$^3$H]nicotine used in all experiments was purified chromatographically by the method of Romm, et al., *Life Sci.*, Vol. 46, pp. 935–943 (1990). The binding of L-[$^3$H]nicotine was measured using a 2 hr. incubation at 4° C. Incubations contained about 500 ug of protein and were conducted in 12 mm×75 mm polypropylene test tubes in a final incubation volume of 250 ul. The incubation buffer was Krebs-Ringers HEPES containing 200 mM TRIS buffer, pH 7.5. The binding reaction was terminated by filtration of the protein containing bound ligand onto glass fiber filters (Micro Filtration Systems) that had been soaked in buffer containing 0.5 percent polyethyleneimine. Filtration vacuum was –50 to –100 torr. Each filter was washed five times with 3 ml of ice-cold buffer. The filtration apparatus was cooled to 2 ° C.

before use and was kept cold through the filtration process. Nonspecific binding was determined by inclusion of 10 uM nonradioactive nicotine in the incubations.

The inhibition of L-[$^3$H]nicotine binding by test compounds was determined by including one of eight different concentrations of the test compound in the incubation. Inhibition profiles were measured using 10 nM L-[$^3$H]nicotine and IC$_{50}$ values were estimated as the concentration of compound that inhibited 50 percent of specific L-[$^3$H]nicotine binding. Inhibition constants (Ki values), reported in nM, were calculated from the IC$_{50}$ values using the method of Cheng et al., *Biochem. Pharmacol.*, Vol. 22, pp. 3099–3108 (1973).

Determination of Dopamine Release

Dopamine release was measured by preparing synaptosomes from the striatal area of rat brain obtained from Sprague-Dawley rats generally according to the procedures set forth by Nagy et al., *J. Neurochem.*, Vol. 43, pp. 1114–1123 (1984). Striata from 4 rats were homogenized in 2 ml of 0.32M sucrose buffered with 5 mM HEPES (pH 7.5), using a glass-Teflon tissue grinder. The homogenate was diluted to 5 ml with additional homogenization solution and centrifuged at 1,000×g for 10 min. This procedure was repeated on the new pellet and the resulting supernatant was centrifuged at 12,000×g for 20 min. A 3 layer discontinuous Percoll gradient consisting of 16 percent, 10 percent and 7.5 percent Percoll in HEPES-buffered sucrose was made with the final pellet dispersed in the top layer. After centrifugation at 15,000×g for 20 min., the synaptosomes were recovered above the 16 percent layer with a Pasteur pipette, diluted with 8 ml of perfusion buffer (128 mM NaCl, 2.4 mM KCl, 3.2 mM CaCl$_2$, 1.2 mM KH$_2$PO$_4$, 1.2 mM MgSO$_4$, 25 mM HEPES pH 7.4, 10 mM dextrose, 1 mM ascorbate, 0.01 mM pargyline), and centrifuged at 15,000×g for 20 min. The new pellet was collected and re-suspended in perfusion buffer. The synaptosome suspension was incubated for 10 min. at 37 ° C. [$^3$H]-Dopamine (Amersham, 40–60 Ci/mmol) was added to the suspension to give a final concentration of 0.1 uM, and the suspension was incubated for another 5 min. Using this method, 30 to 90 percent of the dopamine was taken up into the synaptosomes, as determined by scintillation counting following filtration through glass fiber filters soaked with 0.5 percent polyethyleneimine. A continuous perfusion system was used to monitor release following exposure to each ligand. Synaptosomes were loaded onto glass fiber filters (Gelman type A/E). Perfusion buffer was dripped onto the filters (0.2–0.3 ml/min.) and pulled through the filters with a peristaltic pump. Synaptosomes were washed with perfusion buffer for a minimum of 20 min. before addition of the ligand. After the addition of 0.2 ml of a solution containing various concentrations of ligand, the perfusate was collected into scintillation vials at 1 min. intervals and the dopamine released was quantified by scintillation counting. Peaks of radioactivity released above background were summed and the average basal release during that time was subtracted from the total. Release was expressed as a percentage of release obtained with an equal concentration of (S)-(–)-nicotine.

Determination of Interaction with Muscle

Human muscle activation was established on the human clonal line TE671/RD which is derived from an embryonal rhabdomyosarcoma (Stratton et al., *Carcinogen*, Vol. 10, pp. 899–905 (1989)). As evidenced through pharmacological (Lukas, *J. Pharmacol. Exp. Ther.*, Vol. 25 1, pp. 175–182 (1989)), electrophysiological (Oswald et al, *Neurosci. Lett.*, Vol. 96, pp. 207–212 (1989)), and molecular biological studies (Luther et al., *J. Neurosci.*, Vol. 9, pp. 1082–1096

(1989)) these cells express muscle-like nicotinic receptors. Nicotinic acetylcholine receptor (nAChR) function was assayed using $^{86}Rb^+$ efflux according to a method described by Lukas et al., Anal. Biochem., Vol. 175, pp. 212–218 (1988). Dose-response curves were plotted and the concentration resulting in half maximal activation of specific ion flux through nicotinic receptors determined for human muscle and rat ganglionic preparations (EC50). The maximal activation for individual compounds (Emax) was determined as a percentage of the maximal activation induced by (S)-(−)-nicotine.

Determination of Interaction with Ganglia

Ganglionic effects were established on the rat pheochromocytoma clonal line PC12, which is a continuous clonal cell line of neural crest origin derived from a tumor of the rat adrenal medulla expressing ganglionic-type neuronal nicotinic receptors (see Whiting et al., Nature, Vol. 327, pp. 515–518 (1987); Lukas, J. Pharmacol. Exp. Ther., Vol. 251, pp. 175–182 (1989); Whiting et al., Mol. Brain Res., Vol. 10, pp. 61–70 (1990)). Discussion concerning the heterogeneity of nicotinic receptors subtypes is set forth in Lukas et al., Internatl. Review Neurobiol., Vol. 34, pp. 25–130 (1992). Acetylcholine nicotinic receptors expressed in rat ganglia share a very high degree of homology with their human counterparts. See, Fornasari et al., Neurosci. Lett., Vol. 111, pp. 351–356 (1990) and Chini et al., Proc. Natl. Acad. Sci. USA, Vol. 89, pp. 1572–1576 (1992). Both clonal cell lines described above were maintained in proliferative growth phase according to routine protocols (Bencherif et al., Mol. Cell. Neurosci., Vol. 2, pp. 52–65, (1991) and Bencherif et al., J. Pharmacol. Exp. Ther., Vol. 257, pp. 946–953 (1991)). Intact cells on dishes were used for functional studies. Routinely, sample aliquots were reserved for determination of protein concentration using the method of Bradford, Anal. Biochem., Vol. 72, pp. 248–254 (1976) with bovine serum albumin as the standard.

Nicotinic acetylcholine receptor (nAChR) function was assayed using $^{86}Rb^+$ efflux according to a method described by Lukas et al., Anal. Biochem., Vol. 175, pp. 212–218 (1988). Cells were plated in 35-mm diameter wells of 6-well dishes for at least 48 hours and loaded for at least 4 hours at 37° C. in a medium containing serum, and 1 µCi/ml $^{86}Rb^+$. Following removal of the loading medium, cells were quickly washed three times with label-free Ringer's solution and exposed for 4 minutes at 20° C. to 900 µl of Ringer's containing the indicated concentration of compound to be tested (to define total efflux) or in addition to 100 µM mecamylamine (to define non-specific efflux). The medium was removed and $^{86}Rb^+$ was quantitated using Cerenkov detection (see Lukas et al., Anal. Biochem., Vol. 175, pp. 2 12–218 (1988)). Specific ion efflux was determined as the difference in isotope efflux between total and non-specific efflux samples. Dose-response curves were plotted and the concentration resulting in half maximal activation of specific ion flux through nicotinic receptors determined for human muscle and rat ganglionic preparations (EC50). The maximal activation for individual compounds (Emax) was determined as a percentage of the maximal activation induced by (S)-(−)-nicotine.

Data are presented in Table 1.

TABLE I

| Sample No. | Ki (nM) | Dopamine Release EC50 (nM) | Dopamine Release Emax (% nicotine) | Muscle Effect (% nicotine) | Ganglion Effect (% nicotine) |
| --- | --- | --- | --- | --- | --- |
| C-1* | 2 | 115 | 100 | 100 | 100 |
| 1 | 269 | 4360 | 113 | 0 | 0 |
| 2 | 86 | 5800 | 77 | 4 | 1 |
| 3 | 22 | 4000 | 95 | 0 | 0 |
| 4 | 58 | 8350 | 87 | 7 | 59 |
| 5 | 77 | 11339 | 88 | 0 | 0 |
| 6 | 176 | 219 | 60 | 2 | 4 |
| 7 | 910 | ND | 72 | 0 | 31 |
| 8 | 16 | 1470 | 80 | 15 | 0 |

*not an example of the invention
ND = not determined

The data in Table I indicate that the compounds of the present invention have the capability to provide treatment of patients susceptible to UC or suffering from UC. The compounds bind to relevant nicotinic receptors, thus demonstrating known nicotinic pharmacology. Compounds having nicotinic pharmacology are expected to cause amelioration of the symptoms of UC. The compounds of the present invention act to cause release of dopamine from striatal tissue. This release of dopamine is expected to cause dopaminergic regulation of rectal blood flow, and hence provide the potential to alleviate the symptoms of UC. The compounds of the present invention, in the therapeutic amounts used, do not cause any appreciable effects at muscle sites and ganglionic sites, thus indicating a lack of undesirable side effects by those compounds.

What is claimed is:

1. A method for providing prevention or treatment of an inflammatory bowel disease, the method comprising administering to a subject an effective amount of a compound having the formula:

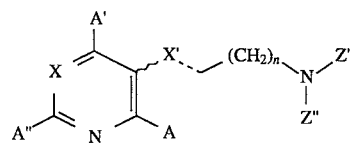

where X is nitrogen or carbon bonded to a substituent species characterized as having a sigma m value between about −0.3 and about 0.75; n is an integer which ranges from 1 to 5; Z' and Z" individually represent hydrogen or alkyl containing one to five carbon atoms; A, A' and A" individually represent hydrogen, alkyl containing one to seven carbon atoms, or halo; the dashed line in the structure represents a C—C single bond, a C—C double bond or a C—C triple bond; the wavy line in the structure represents a cis (Z) or trans (E) form of the compound when the dashed line is a C—C double bond; and X' represents $CH_2$ when the dashed line is a C—C single bond, CH when the dashed line is a C—C double bond, and C when the dashed line is a C—C triple bond.

2. The method of claim 1 whereby the inflammatory bowel disease is ulcerative colitis.

3. The method of claim 1 or 2 whereby the compound is (E)-4-(3-(5-methoxypyridin)yl)-3-butone-1-amine or (E)-N-methyl-4-(3-(5-methoxypyrindin)yl)-3-butene-1-amine.

4. The method of claim 1 or 2 whereby the compound is (E)-metanicotine.

5. The method of claim 1 or 2 whereby the compound is (Z)-metanicotine.

6. The method of claim 1 or 2 whereby the compound is N-methyl-4-(3-pyridinyl)-3-butyne-1-amine.

7. The method of claim 1 or 2 whereby the compound is (E)-N-methyl-4-(3-(6-methylpyrindin)yl)-3-butene-1-amine.

8. The method of claim 1 or 2 whereby the compound is N-methyl-(3-pyridinyl)-butane-1-amine.

9. The method of claim 1 or 2 whereby the compound is (E)-4-(5-pyrimidinyl)-3-butene-1-amine or (E)-N-methyl-4-(5-pyrimidinyl)-3-butene-1-amine.

10. The method of claim 1 or 2 whereby the effective amount of compound administered is amount of at least about 1 mg/24 hr./subject and does not exceed about 500mg/24 hr./subject.

11. The method of claim 1 or 2 whereby the effective amount of compound administered is amount of at least about 10 mg/24 hr./subject and does not exceed about 400 mg/24 hr./subject.

12. The method of claim 10 whereby the effective amount of compound administered is such that the subject does not experience a concentration of compound in plasma which does not exceed 500 ng/ml.

13. The method of claim 1 or 2 whereby X is nitrogen or carbon bonded to a substituent species characterized as having a sigma m value greater than 0; n is an integer which ranges from 1 to 3; Z' and Z" individually represent hydrogen, methyl or isopropyl; A and A' represent hydrogen; and A" represents hydrogen, methyl or ethyl.

14. The method of claim 1 or 2 whereby X is nitrogen or carbon bonded to a substituent species characterized as having a sigma m value less than 0; n is an integer which ranges from 1 to 3; Z' and Z" individually represent hydrogen, methyl or isopropyl; A and A' represent hydrogen; and A" represents hydrogen, methyl or ethyl.

15. The method of claim 1 or 2 whereby n is an integer which ranges from 1 to 3; Z' and Z" individually represent hydrogen, methyl or isopropyl; A and A' represent hydrogen; A" represents hydrogen, methyl or ethyl; and when the dashed line is a C—C double bond and the compound has the trans (E) form, the substituent species is characterized as having a sigma m value not equal to 0.

16. The method of claim 1 or 2 whereby X is nitrogen or carbon bonded to a substituent species characterized as having a sigma m value between about −0.25 and about 0.6; n is an integer which ranges from 1 to 3; Z' and Z" individually represent hydrogen, methyl or isopropyl; A and A' represent hydrogen; and A" represents hydrogen, methyl or ethyl.

17. The method of claim 1 or 2 whereby X is nitrogen; n is an integer which ranges from 1 to 3; Z' and Z" individually represent hydrogen, methyl or isopropyl; A and A' represent hydrogen; and A" represents hydrogen, methyl or ethyl.

18. The method of claim 1 or 2 whereby X is nitrogen or carbon bonded to hydrogen; A and A' represent hydrogen; and A" represents hydrogen, methyl or ethyl.

19. The method of claim 1 or 2 whereby the dashed line in the structure represents a C—C single bond and X' represents $CH_2$.

20. The method of claim 1 or 2 whereby the dashed line in the structure represents a C—C double bond, the wavy line in the structure represents the cis(Z) or trans(E) form of the compound, and X' represents CH.

21. The method of claim 1 or 2 whereby the dashed line in the structure represents a C—C triple bond and X' represents C.

* * * * *